United States Patent [19]

Packman

[11] Patent Number: 4,945,084

[45] Date of Patent: Jul. 31, 1990

[54] METHOD AND COMPOSITION FOR TOPICALLY TREATING ANORECTAL OR OTHER DERMAL WOUNDS

[75] Inventor: Elias W. Packman, Merion, Pa.

[73] Assignee: Norman Oksman, Mountain Lakes, N.J.

[21] Appl. No.: 70,904

[22] Filed: Jul. 8, 1987

[51] Int. Cl.$^5$ .......................................... A61K 31/715
[52] U.S. Cl. ..................................... 514/53; 514/882
[58] Field of Search ................................. 514/53, 882

[56] References Cited

U.S. PATENT DOCUMENTS

| RE. 28,011 | 5/1974 | Urbin | 424/94 |
|---|---|---|---|
| 3,432,489 | 3/1969 | Nitta et al. | 514/927 X |
| 3,935,310 | 1/1976 | Homan | 424/195 |
| 4,192,866 | 3/1980 | Anderson | 425/154 |
| 4,613,498 | 9/1986 | Crosby | 514/882 X |
| 4,626,433 | 12/1986 | Gros | 514/882 X |

FOREIGN PATENT DOCUMENTS

| 1218601 | 3/1987 | Canada | 167/123 |
|---|---|---|---|
| 0230023 | 7/1987 | European Pat. Off. | |

OTHER PUBLICATIONS

Federal Register, May 27, 1980, 45 35576-35677.
The Merck Index, 10th Edition, 1983, Merck and Co., Inc., Rahway, N.J., p. 1273, at 8755.
Borrers et al., American Journal of Surgery, 1984, pp. 809-812.
Halter, F., South African Medical Journal, 1984, pp. 996-1000.
Physicians' Desk Reference, 43rd Edition, 1989, pp. 1214-1215.
Hodes, Benjamin, Handbook of Non-Prescription Drugs, Hemorrhodial Products, 7th Editiion, American Pharmaceutical Association, 1982, pp. 645-655.
Martindale, The Extra Pharmacopeia, 28th Edition, 1983, p. 84.
Remington's Pharmaceutical Sciences, 17th Edition, 1985, p. 815.
Solomon, Margaret A., Oral Sucralfate Suspension for Mucositis, The New England Journal of Medicine, 1986, pp. 459-460.
The American Journal of Medicine, vol. 83, 1987, pp. 1-127.

*Primary Examiner*—Leonard Schenkman
*Attorney, Agent, or Firm*—Weiser & Stapler

[57] ABSTRACT

Hemorrhoidal compositions containing disaccharide polysulfate-aluminum compounds such as sucralfate, alone or in combination with other hemorrhoidal products, as an agent effective for alleviating the symptoms of anorectal disease when topically applied to the human skin. Method for alleviating the symptoms of hemorrhoids in humans. Compositiions containing disaccharide polysulfate-aluminum compounds such as sucralfate, alone or in combination with antibiotics, antifungal agents, anti-acne agents, or local anesthetics as an active agent effective in promoting the healing of wounds which are not anorectal when topically applied to the surface of a wound. Method for promoting healing at the surface of a wound in humans.

34 Claims, No Drawings

METHOD AND COMPOSITION FOR TOPICALLY TREATING ANORECTAL OR OTHER DERMAL WOUNDS

This invention relates to a method and medication for the treatment of wounds and lesions. It further relates to a method and medication for the treatment of the symptoms of anorectal disease or irritation and in particular relates to a method and medication for the treatment of hemorrhoids.

Anorectal disease is an annoying and uncomfortable disorder. Hemorrhoids is a common ailment of the anorectal area and may be either or both internal and external. Anorectal disorders are characterized by the signs and symptoms of itching, burning, pain, bleeding, seepage, protrusion, inflammation, irritation, swelling general discomfort and changes in bowel pattern or any combination thereof. Many remedies have been suggested and tied for the alleviation of these ailments with varying degrees of success. Anorectal disease, though rare in other animals, is very common in humans. No human is immune. The vast majority of adults suffer from one or more anorectal symptoms at some time in their life. Anorectal disease has caused an unaccountable number of man-hours to be lost annually in the work place.

Compositions have previously been developed which generally relieve either the itching or inflammation but few have been successful in reducing or completely eliminating both. Thus, the efficacy of these compositions in relieving or curing the symptoms of such diseases is uncertain.

Some of the compositions disclosed to be useful in the treatment of hemorrhoids include a powdered mixture of alum, quinine sulfate and aspirin mixed with petroleum jelly (U.S. Pat. No. 4,613,498); a mixture of oxidase enzymes (U.S. Pat. RE No. 28,011); a mixture of the powdered or chipped limbs or roots of the shrub *Celastrus scandens* (U.S. Pat. No. 3,935,310); a mixture of polyglycerides and ripe berry products of the plant *Solanum carolinese* to which sublimed sulfur, ammonium alum and turpentine are added (U.S. Pat. No. 4,192,866). Other compositions, which are well known, include those marketed over-the-counter. Non-limiting examples of these numerous products of varying compositions include Anusol, Balneol, Lanacane, Nupercainal, Preparation H and Vaseline.

The FDA has published a monograph relating to Anorectal Drug Products for over-the-counter human use: the proposed monograph was published at Federal Register 45 35576, May 27, 1980. The monograph lists over 75 ingredients which are contained in marketed products submitted to the FDA panel for review. The ingredients are classified as being local anesthetics, vasoconstrictors, protectants, counterirritants, astringents, wound-healing agents, antiseptics, keratolytics and anticholinergics. The composition used in this invention is not listed in the monograph.

It is evident that numerous attempts have been made to solve the problem of the treatment of hemorrhoids and yet no entirely satisfactory solution is yet available. There is a real need for a safe and effective product and treatment for the relief and cure of anorectal disease.

It is, therefore, an object of the present invention to provide a preparation for use in the treatment of anorectal disease and irritation.

It is another object of the present invention to provide a preparation which reduces swelling, inflammation and pain caused or attributable to anorectal disease.

It is a further object of the instant invention to provide a method for treating the symptoms of anorectal disease to control or relieve such symptoms at a wound site.

Another object of the present invention is the relief of the symptons of anorectal disease, like inflammation, irritation, itching and the accompanying or consequential psychological and/or emotional effects.

Another object of the instant invention is to provide a preparation which combines with damaged tissue, (where such exists) to form a protective barrier over a wound or lesion.

A further object of the instant invention to provide a preparation which forms a protective barrier for a wound and also acts as a carrier for materials such as antibiotics, local anesthetics, antihistamines, antiacne materials and antifungal materials.

The invention provides a method for treating the symptoms of anorectal disease by topically administering to the perianal region of a human body, in an amount effective to control or relieve such symptoms, a composition which is safe and effective and includes as an active ingredient a disaccharide polysulfate-aluminum compound.

This invention provides a composition and a method for treating dermal wounds or lesions which are not caused by conditions of high acidity or chemotherapy.

The composition of the instant invention comprises a disaccharide polysulfate-aluminum compound such as sucralfate in combination with a pharmaceutically acceptable carrier. The composition is typically dispersed in a topical medium as the carrier of choice.

It is known to one skilled in the art that the use of disaccharide polysulfate-aluminum compounds is an accepted medical treatment for peptic ulcer. Such compounds are disclosed in U.S. Pat. No. 3,432,489 to Nitta et al (Nitta), which is incorporated herein by reference. Typical compounds are sucrose polysulfate-aluminum compounds, lactose polysulfate-aluminum compounds and maltose polysulfate-aluminum compounds. The sulfur and aluminum contents are commonly in the range of 7–13% and 11–24%, respectively and, therefore, generally contain 1–4 aluminum atoms per sulfur atom.

Nitta discloses the internal use of these compounds in the treatment of peptic ulcers by oral administration. The disaccharide polysulfate-aluminum compounds are hardly absorbed in the digestive tract. The dosage of the compounds in human beings is disclosed to be preferably between 2 and 12 g per day administered divided into several doses. Each unit dose preferably contains between 500 and 1000 mg of the compound along with the carrier or excipient.

One of the compounds disclosed in Nitta is a sucrose polysulfate aluminum compound referred to in The Merck Index, Merck & Co., Inc., Rahway, NJ, 10th Edition, 1983 at number 8755 as sucralfate. This compound is currently marketed as an anti-ulcerative agent. The disaccharide polysulfate-aluminum complexes are referred to hereinafter for the purposes of simplicity as sucralfate. When sucralfate is mentioned, all disaccharide polysulfate-aluminum compounds are intended to be within the scope of the invention.

When, as disclosed by Nitta, sucralfate was administered orally to rats whose pylorus was ligated according to Shay's method, the development of Shay rat ulcer was suppressed. In addition, the development of histamine-induced ulcer in guinea pig was suppressed by the administration of sucralfate.

Nitta also discloses that human patients having gastric or duodenal ulcers were given oral administration of sucralfate. All patients experienced curing effects of the compound.

Peptic ulcer is a pathology characterized by erosion of the mucosa. The mucosa is located anatomically in areas bathed by acid. The major areas where mucosa occurs include the esophagus, the stomach (gastric mucosa) and the duodenum (duodenal mucosa).

Nitta teaches that the pH of gastric juices in the mouse ranges from about 1.0 to 4.0. Sucralfate was shown to have an antacid effect. Therefore, sucralfate is understood to work in areas of high acidity, more particularly at a pH of about 1.5 to about 3.5. The use of acid neutralizing substances such as antacids are contraindicated for administration with sucralfate since such substance would tend to lessen, if not cancel out, the effect of the sucralfate. The literature and medical practice therefore suggest that the benefit of sucralfate is optimally obtained in an acidic medium.

Sucralfate is now recognized by those skilled in the art as being comparable to cimetidine in the treatment of peptic ulcer disease (Borrers et al, Am. J. Surg., 148 (1984) pp 809–12) and in short term duodenal and gastric ulcer healing (Halter, S. Afr. Med. Journal 23 (1984) 996–1000).

In addition, oral ulcers or mucositis which have developed as a direct consequence of treatment of patients receiving chemotherapy or radiation or both have been treated with sucralfate suspension with some success. (Solomon, Cell 351, 459 (August, 1986).

In contrast, the wounds, lesions, inflammations, etc. which are treated in accordance with the instant invention are not associated with or caused by condition of high acidity or by reaction to a chemical agent (chemotherapy).

Anorectal disease, including hemorrhoids, is concerned with three parts of the body, the perianal area, the anal canal and the rectum. The causes of hemorrhoids include predisposing causes such as erect posture, heredity, occupation and diet and precipitating causes such as constipation, diarrhea, pregnancy, anal infection, rectal carcinoma, pelvic tumors, cardiac failure, portal hypertension, coughing, sneezing, vomiting and physical exertion. Hemorrhoids are abnormally large or symptomatic conglomerates of blood vessels, supporting tissues and overlying mucous membrane or skin of the anorectal area. In addition to hemorrhoids, other anorectal disorders which are treated in accordance with the instant invention include anal fistulas and anal fissures.

Essentially, the condition of anorectal disease is not affected by pH or acidity. In fact, the pH within the anorectal region is very different than that which prevails in the stomach. The pH in the human stomach is generally below 4.0 and commonly in the range of 1.0 to about 2.0. Gastric juice analysis has a pH of about 1.0 to 4.0 (see Nitta). The pH in the anorectal region is close to neutrality, typically between about 6 and about 7. The rectal pH ranges from neutral to basic. Therefore, anorectal disease is not associated with low pH or acidic secretion and acid neutralizing materials have no effect on the progression control or retarding of anorectal disease.

It was thus unexpected that the administration of sucralfate aids in the relief of the symptoms of anorectal disease.

The symptoms of anorectal disease which are relieved by the method of treatment and composition of the instant invention include itching, burning, pain inflammation, irritation, swelling, discomfort and bleeding. In addition, the size of a hemorrhoid can be reduced by treatment with the compositions of the invention.

The compositions of the invention are applied topically to the anorectal area to obtain relief from the above mentioned symptoms. Depending on the particular symptom, the administration is on any or all of the regions of the anorectal area including the perianal area or portion of the skin and buttocks immediately surrounding the anus, the modified anal skin area of the anal canal and the mucous membrane of the rectum.

The compositions are applied topically to the involved area until the symptoms are relieved. The compositions are administered once or several times over the course of a single day. The administration is continued for as many days as are necessary to relieve the condition being treated.

The amounts of sucralfate which is administered in accordance with the invention is noteworthy. Particularly, it has been noted in accordance with the invention that the compositions of the invention form a visible complex of the white sucralfate with the inflamed and damaged area. Thus the compositions make available prolonged and extended treatment.

In the composition of the invention the sucralfate is present in an amount from about 0.1% to 25% but it can be present in smaller amounts like 0.01% to less than 0.1% or in amounts over 25% to 50%.

The unit dose administered is in the range of from 0.01 to 1.0 g per dose not to exceed about 5 g in a 24 hour period. Preferably the unit dose is from about 0.05 to 0.5 g per dose, although the unit dose can be adjusted upward or downward as warranted by the size of the area being treated.

When an ointment containing 5% sucralfate was applied topically to the anorectal region of subjects suffering from hemorrhoids immediately before and immediately after defecation, the subjects immediately experienced relief from pain. In addition, after 5 days, bleeding and the size of the hemorrhoid were decreased.

It was observed that the white ointment containing the sucralfate adhered to the hemorrhoid even after defecation. No adherence was observed when the same ointment without sucralfate was applied. Thus, this was a visual demonstration that complexing occurred between the sucralfate and the inflamed and damaged area. Unexpectedly, this complex formation occurred in a non-acidic environment.

In another embodiment of the invention the sucralfate is administered to a patient with the symptoms of anorectal disease in conjunction with the administration of a product therapeutically helpful in the symptomatic treatment of anorectal disease. Examples of over-the-counter products which can be administered with sucralfate include but are not limited to, A-Caine, Americaine, Anusol, Balneol, BiCozene, Blue-Gray, Calmol 4, Cortef Rectal Itch Ointment, Diothane, Epinephricaine Ointment, Gentzy Wipes, Hemorrin, HTO Ointment, HTO Stainless, Lanacane, Mediconet, Non-Steroid Proctofoam, Nupercainal Ointment, Nupercainal Suppositories, Pazo, Perifoam, Peterson's Ointment, Pontocaine, Preparation H, Preparation H Cleansing Pads, Proctodon, Rantex, Rectal Medicone Suppositories, Rectal Medicone Unquent, Tanicaine Ointment, Tanicaine Suppositories, Tronolane, Tucks Cream and Ointment, Tucks Pads, Vaseline Pure Petroleum Jelly, Wyanoid Ointment and Wyanoid Suppositories. See also Federal Register, 45 33576, May 22, 1980.

The main pharmacologic agents formulated in the above products include local anesthetics, vasoconstrictors, protectant, counterirritants, astringents, wound healing agents, antiseptics, keratolytics and anticholinergics. See also Federal Register 45 35576, May 27, 1980. It is within the scope of the instant invention that sucralfate is administered in combination with any or all of these agents. Preferred agents include those known as topical anesthetics, protectants, vasoconstrictors and wound healing agents.

Local or topical anesthetics temporarily relieve pain, burning, itching, discomfort and irritation by preventing transmission of nerve impulses. Non-limiting examples of topical anesthetics include benzocaine, pramoxine hydrochloride, benzyl alcohol, dibucaine hydrochloride, dicylonine hydrochloride, lidocaine, tetracaine and tetracaine hydrochloride. See also Federal Register, 45 35576, May 27, 1980. Preferred are benzocaine and pramoxine hydrochloride which are generally recognized as being safe and effective.

Protectants act to prevent irritation of the anorectal area and water loss from the skin layer by forming a physical barrier on the skin. There is little or absorption of the protectants. Non-limiting examples include aluminum hydroxide gel, calamine, cocoa butter, cod liver oil, glycerin, kaolin, lanolin, mineral, shark liver oil, starch, white petrolatum, wood alcohol and zinc oxide. See also Federal Register, 45 35576, May 27, 1980.

Vasoconstrictors act to reduce inflammation, irritation and swelling by constricting the symptomatic abnormally large conglomerates of blood vessels. Non-limiting examples include ephedrine and epinephrine. See also Federal Register, 45 35576, May 27, 1980.

In non-prescription hemorrhoidal products, several ingredients are claimed to be effective in promoting wound healing or tissue repair in anorectal disease. Non-limiting examples of wound healing agents include skin respiratory factor (SRF), a water soluble extract of brewer's yeast also referred to as live yeast cell derivative, cod liver oil, vitamin A and vitamin D. See Also Federal Register, 45 35576, May 27, 1980.

It is within the scope of the instant invention that sucralfate be administered to a patient having the symptoms of anorectal disease in a separate composition administered in conjunction with the administration of a known composition for the treatment of anorectal disease. Thus, in one embodiment the composition containing sucralfate is administered to the patient immediately before or after the administration of the hemorrhoidal product. In another embodiment the administration of the two compositions is alternated so that several minutes or hours pass before the administration of the second composition.

In another embodiment of the invention sucralfate and other pharmacologic agents used in the treatment of the symptoms of anorectal disease are formulated in the same composition, for example with a wound healing agent, a protectant, a vasoconstrictor, or a local anesthetic or with more than one of these agents.

In a more particular embodiment within the scope of the invention, sucralfate is mixed with an existing product for the treatment of anorectal disease. For example, sucralfate is mixed with Preparation H to obtain a composition of the invention.

It is also within the scope of the instant invention that a pharmaceutical composition containing sucralfate be administered topically to wounds or lesions which are other than anorectal. What is characteristic of these wounds or lesions is that they are of the type which is known to be treated topically.

The wounds or lesions can be caused by infections such as a fungal infection. An example is the lesion caused by athlete's foot. Additionally the wounds or lesions can be caused by allergic reaction, such as that caused by poison ivy, poison oak or poison sumac, or caused by infection or aggravation of another condition such as occurs with acne. The wound can also be caused by physical trauma to the site of the wound to cause a cut, incision or abrasion.

In a particular embodiment of the invention, topical administration of a composition containing sucralfate is used to promote the healing of abrasions such as those which are topically received as a result of physical trauma to joints such as knees, elbows, knuckles, shoulders, hips, shins and the like.

The composition of the invention is applied topically to the involved area until the wound has healed. The compositions are administered once or several times a day for from one day to a week or more until the healing occurs.

In the composition of the invention the sucralfate is present in an amount from about 0.1% to 25% but it can be present in smaller amounts like 0.01% to less than 0.1% or in amounts over 25% to 50%.

The unit dose administered is in the range of from 0.01 to 2.0 g per dose not to exceed about 10 g in a 24-hour period. Preferably the unit dose is from about 0.05 to 0.5 g per dose, although the unit dose can be adjusted upward or downward as warranted by the size of the area being treated.

In a non-limiting example of this embodiment, knee abrasions on basketball players which were caused by falls during a basketball game were treated with an ointment containing 5% sucralfate. The applied white ointment could still be observed on the wounded area 24 hours after the first application. The ointment was reapplied daily. Fusion was stopped after twenty four hours and good healing occurred over a three day period.

It was observed that with each topical application of a sucralfate containing ointment to a wound, anorectal or otherwise, the sucralfate formed a visible complex with the tissue associated with the wound. Thus a further embodiment of the invention is the use of the composition containing sucralfate as a carrier composition for an additional pharmaceutical compound or compounds. The sucralfate complexes with the wounded area thereby holding the additional pharmaceutical compound near the wound. In this manner for example, an antibiotic, a steroid, an antifungal agent, a biocidal agent, a local anesthetic or an anti-acne agent or a combination thereof is applied topically to a wound or lesion site in a composition containing sucralfate and is kept in place by the complexing action of the sucralfate with the tissues in the wound or lesion area.

For the topical treatment of the anorectal and non anorectal wounds the compositions are in the form of ointments, creams, gels, pastes, suppositories, pads, liquids, foams or aerosols or any other composition suitable for topical administration.

In other aspects, the composition of the invention may contain conventional materials and ingredients and conform to pharmacologically accepted formulations.

Carriers into which the active ingredients can be incorporated to produce satisfactory composition are those commonly employed for topical application of cosmetics or pharmaceuticals. Such carriers or vehicles incude lotions, ointments, aerosols, water solutions, creams (preferably of the oil-in-water type), pulverulent mixtures, gelled sticks and the like. Depending on the physical nature of the vehicle or carrier employed, the method of this invention can be practiced by applying such compositions topically in any appropriate manner according to the particular type of carrier employed.

In preparing the desired pharmaceutical form of the present compositions, various additives, diluents and adjuvants can be utilized. These illustratively include perfumes, essential oils, surfactants, ointment type bases, higher fatty acids, propellants, thickening agents, humectants, silicone-type fluids and solid diluents as is known in the art.

The following examples are not intended to limit the invention but are merely illustrative thereof. It is understood that one of average skill in the art would be able to make substitutions, change proportions, make other variations, all within the scope of the teachings and without departing from the spirit of the invention and without undue experimentation.

EXAMPLE 1

Ointment

An ointment was formulated by mixing the following ingredients:

| Ingredient | % by Weight |
| --- | --- |
| Stearic Acid | 7 |
| Cetyl Alcohol | 2 |
| Mineral Oil | 20 |
| Glycerin | 10 |
| Triethanolamine | 2 |
| Purified Water qs | 100 |

To this ointment, there is added sucralfate to obtain a 5% final concentration.

EXAMPLE 2

Gel

A gel composition was prepared by mixing the following ingredients:

| Ingredient | % by Weight |
| --- | --- |
| Samuet | 0.3 |
| Purified Water qs. | 100 |

To this gel there is added sucralfate to obtain a 5% final concentration.

EXAMPLE 3

Cream

A cream was prepared by mixing the following ingredients:
5% Sucralfate
qs. Hydrophylic Ointment

EXAMPLE 4

Suppository

A suppository was formulated by mixing the following ingredients:

| Ingredient | % by Weight |
| --- | --- |
| Polyethylene Glycol 400 | 10 |
| Polyethylene Glycol 1500 | 30 |
| Polyethylene Glycol 6000 | 60 |

To this formulation there is added sucralfate to a final concentration of 5% and the formulation was formed into the desired shape.

EXAMPLE 5

Ointment

An ointment was prepared by mixing the following ingredients:

| Ingredient | % by Weight |
| --- | --- |
| Preparation H | 95 |
| Sucralfate | 5 |

EXAMPLE 6

Ointment

An ointment was formulated by mixing the following ingredients:

| Ingredient | % by Weight |
| --- | --- |
| Stearic Acid | 7 |
| Cetyl Alcohol | 2 |
| Mineral Oil | 20 |
| Glycerin | 10 |
| Triethanol Amine | 2 |
| Benzocaine | 6 |
| Sucralfate | 5 |
| Purified Water | 48 |

EXAMPLE 7

The ointment of Example 1 containing 5% sucralfate was compared for efficacy against hemorrhoids with the same ointment without sucralfate.

The total number of subjects was 6. All subjects were between 55 and 70 years of age and suffered with external hemorrhoids. Symptomatically, all subjects experienced pain and bleeding during defecation. In addition, each suffered from hemorrhoids sufficiently large that they were readily observed and measured.

Three of the subjects were treated with the ointment without sucralfate and three were treated with the ointment containing 5% sucralfate. The ointment was applied immediately before and immediately after defecation in an amount sufficient to cover the perianal area and the anal canal as a thin covering.

Over a 5-day-period, of the three subjects who were treated with the ointment alone, only one experienced some relieve in that there was some reduction of pain and some reduction of bleeding during defecation. The other two subjects had no relief of symptoms and after three days requested a change in treatment because of the lack of relief.

The three subjects who were treated with the 5% sucralfate ointment all reported reduction or absence of pain and reduction or absence of bleeding during defecation. A marked reduction in the size of the external hemorrhoid to almost normal was visually observed. The results are tabulated in Table I.

TABLE I

| Subject # | 5% sucralfate | Response | | |
|---|---|---|---|---|
| | | Pain | Bleeding | Size/Hem. |
| 1 | No | 0 | 0 | 0 |
| 2 | No | 0 | 0 | 0 |
| 3 | No | + | + | 0 |
| 4 | Yes | ++ | ++ | ++ |
| 5 | Yes | ++ | +++ | ++ |
| 6 | Yes | +++ | +++ | ++ |

Scale 0 No relief
+ Some reduction
++ Significant reduction
+++ Complete absence of symptom

EXAMPLE 8

The ointment of Example 5 was applied before and after defecation to a patient suffering from external hemorrhoids as described in Example 7. Relief from the symptoms of pain and bleeding during defecation was obtained and a reduction in the size of the external hemorrhoids was visually observed.

EXAMPLE 9

The ointment of Example 6 was applied before and after defecation to a patient suffering from external hemorrhoids as described in Example 7. Relief from the symptoms of pain and bleeding during defecation was obtained and a reduction in the size of the external hemorrhoids was visually observed.

EXAMPLE 10

Knee abrasions on three adult males, ages 19-21, as the result of a basketball game were treated with the 5% sucralfate ointment of Example 1 as follows.

The wound was cleaned by washing and the 5% sucralfate ointment was applied. The fusion was stopped by the next day in each case. The ointment was reapplied daily. Good healing occurred over a three-day period. Sucralfate could be seen to be present on a wound 24 hours after a single application.

In the above examples, ingredients other than those recited can be added to achieve a desirable pharmaceutical effect. The physical form of the product can be any of those known to the cosmetic art.

The compositions of the invention are administered topically to the site of the wound or lesion once or several times a day depending on the condition which is being treated as is known to one skilled in the art.

This invention provides a composition which is relatively simple to prepare and to apply, and it has been found effective in accomplishing its desired purpose.

Although particular formulations have been shown and described above, modifications may be made, and it is intended in the claims to cover all modifications which come within the spirit and scope of the invention.

I claim:

1. A composition for topical administration in the treatment of an anorectal disease or disorder in humans which comprises a disaccharide polysulfate-aluminum compound and a pharmaceutically-acceptable topical carrier selected from the group consisting of an ointment, cream, gel, paste, foam, aerosol, suppository, pad and gelled stick.

2. The composition of claim 1 wherein the disaccharide polysulfate-aluminum compound is present in an amount from about 0.1 to about 25%.

3. The composition of claim 1 wherein the disaccharide polysulfate-aluminum compound is present in an amount from about 0.1 to about 5%.

4. The composition of claim 1 wherein the disaccharide polysulfate-aluminum compound is selected from the group consisting of sucrose polysulfate-aluminum compounds, lactose polysulfate-aluminum compounds and maltose polysulfate-aluminum compounds, the S and Al contents of which are 7-13% and 11-24%, respectively.

5. The composition of claim 1 wherein the disaccharide polysulfate-aluminum compound is sucralfate.

6. The composition of claim 1, wherein the anorectal disease or disorder is an anorectal wound or lesion.

7. The composition of claim 1, wherein the anorectal disease or disorder is hemorrhoids.

8. The composition of claim 1, wherein the anorectal disease or disorder is an anal fistula or fissure.

9. The composition of claims 1, 2, 3, 4 or 5, wherein the carrier is an ointment, cream, gel, paste, foam, aerosol or suppository.

10. The composition of claim 1 wherein the carrier is an ointment, cream, gel, paste or suppository.

11. The composition of claim 1 wherein the amount of the disaccharide polysulfate-aluminum compound is in the range from about 10 mg to about 2000 mg per dose.

12. The composition of claim 1 wherein the disaccharide polysulfate-aluminum compound ranges in an amount from a dose sufficient to alleviate the disease or disorder to less than 500 mg per dose.

13. The composition of claim 1 wherein the amount of the disaccharide polysulfate-aluminum compound ranges from about 50 mg per dose to less than 500 mg per dose.

14. A composition for topical administration in the treatment of a dermal wound or lesion which comprises an amount of a disaccharide polysulfate-aluminum compound sufficient to alleviate the symptoms caused by a wound or lesion and a pharmaceutically-acceptable topical carrier specifically adapted for topical delivery of the compound to the affected area, said carrier being selected from the group consisting of an ointment, cream, gel, paste, foam, aerosol, pad and gelled stick.

15. The composition of claim 14, further including an antibiotic, an antifungal agent, a steroid, a biocide, a topical anesthetic, or an anti-acne agent.

16. The composition of claim 14 wherein the skin wound or lesion is on a knee, elbow, knuckle, shoulder, hip or shin.

17. An anorectal composition useful for alleviating symptoms of anorectal disease which comprises a pharmaceutically acceptable carrier, a symptom-alleviating amount of a disaccharid polysulfate-aluminum compound and a compound selected from the group consisting of a topical anesthetic, a wound healing agent and a protectant.

18. The composition of claim 17 wherein the disaccharide polysulfate-aluminum compound is present in an amount from about 0.1 to about 25%.

19. The composition of claim 18 wherein the disaccharide polysulfate-aluminum compound is present in an amount from about 0.1 to about 5%.

20. The composition of claim 18 wherein the disaccharide polysulfate-aluminum compound is selected from the group consisting of sucrose polysulfate-aluminum compounds, lactose polysulfate-aluminum compounds and maltose polysulfate-aluminum compounds, the S and Al contents of which are 7–13% and 11–24%, respectively.

21. The composition of claim 17 wherein the disaccharide polysulfate-aluminum compound is sucralfate.

22. The composition of claim 17 wherein the topical anesthetic is selected from the group consisting of benzocaine, pramoxine hydrochloride, benzyl alcohol, dibucaine hydrochloride, dyclonine hydrochloride, lidocaine tetracaine and tetracaine hydrochloride.

23. The composition of claim 17 wherein the wound healing agent is selected from the group consisting of skin respiratory factor (SRF), a live yeast cell derivative, cod liver oil, peruvian balsam, shark liver oil, vitamin A and vitamin D.

24. The composition of claim 17 wherein the protectant is selected from the group consisting of aluminum hydroxide gel, calamine, cocoa butter, cod liver oil, glycerin in aqueous solution, kaolin, lanolin, mineral oil, shark liver oil, starch, white petrolatum, wood alcohol and zinc oxide.

25. A method for alleviating the symptoms of anorectal disease which comprises administering topically to a human an anorectal composition comprising a pharmaceutically-acceptable carrier, an effective amount of a disaccharide polysulfate-aluminum compound and a compound selected from the group consisting of a topical anesthetic, a wound healing agent and a protectant.

26. A method for the treatment of dermal wounds or lesions which comprises administering topically to the wound or lesion area a composition comprising a pharmaceutically-acceptable carrier and an effective amount of a disaccharide polysulfate-aluminum compound.

27. The method of claim 26 wherein the composition is administered in conjunction with a compound selected from the group consisting of an antibiotic, a local anesthetic, an antihistamine, an anti-acne agent a steroid and an antifungal agent.

28. The method of claim 26 wherein the dermal wound is on a knee, elbow, knuckle, shoulder, hip or shin.

29. A method for alleviating the symptoms caused by hemorrhoids in humans which comprises administering topically to a human an anorectal composition comprising a pharmaceutically-acceptable carrier and an effective amount of a disaccharide polysulfate-aluminum compound.

30. The method of claim 29 wherein the disaccharide-polysulfate aluminum compound is selected from the group consisting of sucrose polysulfate-aluminum compounds, lactose polysulfate-aluminum compounds and maltose polysulfate-aluminum compounds, the S and Al contents of which are 7–13% and 11–24%, respectively.

31. The method of claim 29 wherein the disaccharide polysulfate-aluminum compound is sucralfate.

32. The method of claim 29 wherein the anorectal composition is administered in conjunction with a compound selected from the group consisting of a topical anesthetic, a protectant and a wound healing agent.

33. The method of claim 29 wherein the administration is to an area of which has a pH ranging from about neutral to basic.

34. A method for the treatment of a wound or lesion which is not caused by high acidity which comprises administering topically to the wound or lesion area a composition comprising a pharmaceutically-acceptable topical carrier and an effective amount of a disaccharide polysulfate-aluminum compound.

* * * * *

UNITED STATES PATENT AND TRADEMARK OFFICE
CERTIFICATE OF CORRECTION

PATENT NO. : 4,945,084
DATED : July 31, 1990
INVENTOR(S) : Elias W. Packman It is certified that error appears in the above-identified patent and that said Letters Patent is hereby corrected as shown below:

In (73), After "Norman Oksman", insert --(part interest)--

Signed and Sealed this

Twenty-first Day of January, 1992

*Attest:*

HARRY F. MANBECK, JR.

*Attesting Officer*     *Commissioner of Patents and Trademarks*